United States Patent
Hoshino et al.

(10) Patent No.: US 7,341,854 B2
(45) Date of Patent: Mar. 11, 2008

(54) MICROBIAL PRODUCTION OF VITAMIN C

(75) Inventors: Tatsuo Hoshino, Kamakura (JP); Teruhide Sugisawa, Riehen (CH)

(73) Assignee: DSM IP Assets B.V., Heerlen (NL)

( * ) Notice: Subject to any disclaimer, the term of this patent is extended or adjusted under 35 U.S.C. 154(b) by 382 days.

(21) Appl. No.: 10/528,893

(22) PCT Filed: Sep. 22, 2003

(86) PCT No.: PCT/EP03/10494

§ 371 (c)(1),
(2), (4) Date: Mar. 23, 2005

(87) PCT Pub. No.: WO2004/029268

PCT Pub. Date: Apr. 8, 2004

(65) Prior Publication Data

US 2006/0035349 A1    Feb. 16, 2006

(30) Foreign Application Priority Data

Sep. 27, 2002  (EP) ................................. 02021597

(51) Int. Cl.
*C12P 17/04*    (2006.01)

(52) U.S. Cl. ...................................................... 435/126
(58) Field of Classification Search ................. 435/126
See application file for complete search history.

(56) References Cited

U.S. PATENT DOCUMENTS

| 5,250,428 A | 10/1993 | Hoshino et al. |
| 5,312,741 A * | 5/1994 | Hoshino et al. ............... 435/42 |
| 5,437,989 A | 8/1995 | Asakura et al. |
| 6,242,233 B1 * | 6/2001 | Hoshino et al. ............ 435/190 |
| 2001/0026933 A1 * | 10/2001 | Hoshino et al. ............ 435/190 |

FOREIGN PATENT DOCUMENTS

| EP | 0 476 442 A2 | 3/1992 |
| EP | 0 832 974 A2 | 4/1998 |

* cited by examiner

*Primary Examiner*—Herbert J. Lilling
(74) *Attorney, Agent, or Firm*—Bryan Cave LLP

(57) ABSTRACT

The present invention provides a process for the production of vitamin C from different substrates like D-sorbitol, L-sorbose, L-sorbosone or L-gulose using a microorganism selected from the group consisting of *Gluconobacter oxydans* DMS 4025 (FERM BP-3812), a microorganism belonging to the genus *Gluconobacter* and having identifying characteristics of *G. oxydans* DSM 4025 (FERM BP-3812) and mutants thereof.

8 Claims, No Drawings

MICROBIAL PRODUCTION OF VITAMIN C

This application is the National Stage of International Application No. PCT/EP2003/010494, filed Sep. 22, 2003.

The present invention relates to the microbial production of L-ascorbic acid (vitamin C).

Vitamin C, which is one of very important and indispensable nutrient factors for human beings, has been commercially produced by the so-called "Reichstein method", which is well known as a technologically established process. This method, however, comprises a number of complex steps and any improvement in the overall yield is difficult to achieve. Therefore, there have been a number of proposals, which contemplate a reduction in the number of steps and/or an improvement in the overall yield.

The present invention provides a process for the production of vitamin C from D-sorbitol, L-sorbose, L-sorbosone or L-gulose by culturing a microorganism selected from the strain *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof, in an aqueous nutrient medium containing D-sorbitol, L-sorbose, L-sorbosone or L-gulose, and isolating and purifying vitamin C from the fermentation medium.

More particularly, the present invention provides a process for the production of vitamin C from D-sorbitol, L-sorbose, L-sorbosone or L-gulose comprising the steps of:

(a) cultivating a microorganism in an aqueous nutrient medium containing D-sorbitol, L-sorbose, L-sorbosone or L-gulose, wherein the migroorganism is selected from the group consisting of *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof, and (b) isolating and purifying vitamin C from the fermentation medium.

In a preferred embodiment, vitamin C is produced from L-gulose or L-sorbosone by the process defined above. A more preferred embodiment is a process for the production of vitamin C from L-gulose comprising the steps of:

(a) cultivating a microorganism in an aqueous nutrient medium containing L-gulose, wherein the microorganism is selected from the group consisting of *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof, and (b) isolating and purifying vitamin C from the fermentation medium.

The present invention also provides a process for the production of vitamin C from D-sorbitol, L-sorbose, L-sorbosone or L-gulose which process comprises contacting a microorganism selected from the strain *G. oxydans* DSM 4025 (FERM BP-3812), a microorganism belonging to the genus *Gluconobacter* and having identifying characteristics of *G. oxydans* DSM 4025 (FERM BP-3812) and mutants thereof with D-sorbitol, L-sorbose, L-sorbosone or L-gulose in a reaction mixture and isolating and purifying vitamin C from the reaction mixture.

More particularly, the present invention is directed to a method for producing vitamin C from D-sorbitol, L-sorbose, L-sorbosone or L-gulose which process comprises contacting a microorganism selected from the strain *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof with D-sorbitol, L-sorbose, L-sorbosone or L-gulose in a reaction mixture and isolating and purifying vitamin C from the reaction mixture.

*G. oxydans* DSM 4025 was deposited at the Deutsche Sammlung von Mikroorganismen und Zellkulturen (DSMZ) in Göttingen (Germany), based on the stipulations of the Budapest Treaty, under DSM No. 4025 on Mar. 17, 1987. The depositor was The Oriental Scientific Instruments Import and Export Corporation for Institute of Microbiology, Academia Sinica, 52 San-Li-He Rd., Beijing, Peoples Republic of China. The effective depositor was said Institute, of which the full address is The Institute of Microbiology, Academy of Sciences of China, Haidian, Zhongguancun, Beijing 100080, People's Republic of China.

Moreover, a subculture of the strain has also been deposited at the National Institute of Advanced Industrial Science and Technology (AIST), Tsukuba Central 6, 1-1-1 Higashi, Tsukuba, Ibaraki 305-8566, Japan, also based on the stipulations of the Budapest Treaty, under the deposit No. FERM BP-3812 on Mar. 30, 1992. The depositor is Nippon Roche K. K., 6-1, Shiba 2-chome, Minato-ku, Tokyo 105-8532 Japan. This subculture may also be used in the present invention.

Mutants of *G. oxydans* DSM 4025 (FERM BP-3812) or a microorganism belonging to the genus *Gluconobacter* and having identifying characteristics of *G. oxydans* DSM 4025 (FERM BP-3812) can be obtained by treating the cells by means of, for instance, ultraviolet or X-ray irradiation, or a chemical mutagen such as nitrogen mustard or N-methyl-n-nitro-N-nitrosoguanidine.

It is understood that "*Gluconobacter* oxydans" also include synonyms or basonyms of such species having the same physico-chemical properties, as defined by the International Code of Nomenclature of Prokaryotes.

Any type of microorganism may be used, for instance, resting cells, acetone treated cells, lyophilized cells, immobilized cells and the like to act directly on the substrate. Any means per se known as a method in connection with the incubation technique for can be adopted through the use of aeration and agitated submerged fermenters is particularly preferred. The preferred cell concentration range for carrying out the reaction is from about 0.01 g of wet cell weight per ml to about 0.7 g of wet cell per ml, preferably from about 0.03 g of wet cell per ml to about 0.5 g of wet cell per ml.

The cultivation can be conducted at a pH of 4.0 to 9.0, wherein a pH value of about 5.0 to 8.0 is preferred. The cultivation period varies depending on the pH, temperature and nutrient medium to be used, and is preferably about 1 to 5 days, most preferably about 1 to 3 days. The preferred temperature range for carrying out the cultivation is from about 13° C. to about 36° C., more preferably from 18° C. to 33° C. A preferred result is obtainable from an incubation which utilizes a liquid broth medium.

Thus, it is one aspect of the present invention to provide a process for the production of vitamin C from D-sorbitol, L-sorbose, L-sorbosone or L-gulose comprising the steps of:

(a) cultivating a microorganism in an aqueous nutrient medium containing D-sorbitol, L-sorbose, L-sorbosone or L-gulose, wherein the microoganism is selected from the group consisting of *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof, and (b) isolating and purifying vitamin C from the fermentation medium;

wherein the process is carried out at a pH in the range of about 4.0 to about 9.0 and in a temperature range from about 13° C. to about 36° C. for 1 to 5 days.

In a preferred embodiment, the process is carried out at a pH in the range of about 5.0 to about 8.0 and at a temperature range from about 18° C. to about 33° C. for 1 to 3 days.

As the nutrient medium for the incubation of the microorganism any aqueous nutrient medium including a carbon source, a nitrogen source, other inorganic salts, small amounts of other nutrients and the like, including minerals and vitamins, which can be utilized by the microorganism may be used. Various nutrient materials which are generally used for the better growth of microorganisms may suitably be included in the medium.

It is usually required that the culture medium contains such nutrients as assimilable carbon sources, for example glycerol, D-mannitol, erythritol, ribitol, xylitol, arabitol, inositol, dulcitol, D-ribose, D-fructose, D-glucose and sucrose in addition to the carbon sources converted to vitamin C; and digestible nitrogen sources such as organic substances, for example, peptone, yeast extract, baker's yeast, urea, amino acids and corn steep liquor. Various inorganic substances may also be used as nitrogen sources, for example nitrates and ammonium salts. Furthermore, the culture medium usually contains inorganic salts, for example magnesium sulfate, potassium phosphate and calcium carbonate.

For the advantageous performance of the incubation, any suitable factor which can promote the formation of the end product may be added to the medium. Such factors include, but are not limited to, solvents, detergents, antifoam, aeration conditions such as oxygen concentration applied to the reaction.

Although the concentration of D-sorbitol, L-sorbose, L-sorbosone or L-gulose may also be varied with the cultivation conditions, a concentration of about 2 to 120 g/L is generally applicable. A concentration of 4 to 100 g/L is preferred.

The vitamin C thus produced and accumulated in the medium or reaction mixture may be separated and purified by any per se known conventional method which suitably utilized the property of the product, and it may be separated as the free acid or as a salt of sodium, potassium, calcium, ammonium or the like.

Specifically, the separation may be performed by any suitable combination or repetition of the following steps: by the formation of a salt, by using differences in properties between the product and the surrounding impurities, such as solubility, absorbability and distribution coefficient between the solvents, by absorption, for example on ion exchange resin. Any of these procedures alone or in combination constitutes a convenient means for isolating the product. The product thus obtained may further be purified in a conventional manner, e.g., by recrystallization or chromatography.

The identification of the vitamin C obtained by the method of this invention may be performed by, for instance, elemental analysis as well as measurement of physicochemical properties such as spectrum of infrared absorption, mass spectrum, NMR and the like.

According to the present invention, the improvement in terms of the reduction in the number of steps is very significant because it leads to a one step pathway directed to the production of the vitamin C from any one of substrates D-sorbitol, L-sorbose, L-sorbosone or L-gulose.

In the following Examples, the process of the present invention will be illustrated in more detail.

EXAMPLE 1

Conversion of D-sorbitol to Vitamin C

One loopful of *G. oxydans* DSM 4025 (FERM BP-3812) grown on the agar medium containing 5.0% D-mannitol, 0.25% $MgSO_4.7H_2O$, 1.75% corn steep liquor, 5.0% baker's yeast, 0.5% urea, 0.5% $CaCO_3$ and 2.0% agar, which was cultivated at 27° C. for 4 days, was inoculated into 5 ml of seed culture medium containing 8.0% D-sorbitol, 5.0% baker's yeast, 0.05% glycerol, 0.25% $MgSO_4.7H_2O$, 1.75% corn steep liquor, 0.5% urea, 1.5% $CaCO_3$ and one drop of antifoam in test tube, and then cultivated at 30° C. with 240 rpm for 20 h on a reciprocal shaker.

3 ml of the seed culture were transferred into 500 ml Erlenmeyer flasks containing 50 ml of the production medium containing 8.0% D-sorbitol, 5.0% baker's yeast, 0.05% glycerol, 0.25% $MgSO_4.7H_2O$, 3.0% corn steep liquor, 1.5% $CaCO_3$ and 0.15% antifoam. The cultivation was carried out at 30° C. with 180 rpm for 45 h on a rotary shaker. Then, the concentration of vitamin C produced was measured by HPLC at a wavelength of 264 nm with the system which was composed of a UV detector (TOSOH UV8000; TOSOH Co., Kyobashi 3-2-4, Chuo-ku, Tokyo, Japan), a dualpump (TOSOH CCPE; TOSOH Co.), an integrator (Shimadzu C-R6A; Shimadzu Co., Kuwahara-cho 1, Nishinokyo, Chukyo-ku, Kyoto, Japan) and a column (YMC-Pack polyamine II; YMC, Inc., 3233 Burnt Mill Drive Wilimington, N.C. 28403, USA), As a result, 118.1 mg/L of vitamin C was produced.

EXAMPLE 2

Conversion of L-sorbose to Vitamin C

One loopful of *G. oxydans* DSM 4025 (FERM BP-3812) grown on the agar medium containing 5.0% D-mannitol, 0.25% $MgSO_4.7H_2O$, 1.75% corn steep liquor, 5.0% baker's yeast, 0.5% urea, 0.5% $CaCO_3$ and 2.0% agar, which was cultivated at 27° C. for 4 days, was inoculated into 5 ml of seed culture medium containing 8.0% L-sorbose, 5.0% baker's yeast, 0.05% glycerol, 0.25% $MgSO_4.7H_2O$, 1.75% corn steep liquor, 0.5% urea, 1.5% $CaCO_3$ and one drop of antifoam in test tube, and then cultivated at 30° C. with 240 rpm for 20 h on a reciprocal shaker.

3 ml of the seed culture were transferred into 500 ml Erlenmeyer flasks containing 50 ml of the production medium containing 8.0% L-sorbose, 5.0% baker's yeast, 0.05% glycerol, 0.25% $MgSO_4.7H_2O$, 3.0% corn steep liquor, 1.5% $CaCO_3$ and 0.15% antifoam. The cultivation was carried out at 30° C. with 180 rpm for 20 h on a rotary shaker. As a result, 407.1 mg/L of vitamin C was produced.

EXAMPLE 3

Production of Vitamin C from D-sorbitol, L-sorbose, L-sorbosone and L-gulose with Resting Cell System

*G. oxydans* DSM 4025 (FERM BP-3812) was cultivated on the agar medium consisting of 8.0% L-sorbose, 0.25% $MgSO_4.7H_2O$, 1.75% corn steep liquor, 5.0% baker's yeast, 0.5% urea, 0.5% $CaCO_3$ and 2.0% agar at 27° C. for 4 days. The cells of *G. oxydans* DSM 4025 (FERM BP-3812) grown on the above medium were transferred into 50 mM potassium phosphate buffer (pH 7.0) and washed twice with the same buffer. The optical density of the cell suspension at 600 nm was 21.9. It contained 0.057 g of wet cell weight per ml.

The reaction mixture (5 ml in test tube) contained the cell suspension and 8.0% D-sorbitol, 8.0% L-sorbose, 0.5% L-sorbosone or 1.0% L-gulose in 50 mM potassium phosphate buffer (pH 7.0). The reaction was started by the inoculation of cell suspension and carried out at 30° C. and with 180 rpm on a reciprocal shaker. The vitamin C content was measured at the reaction time of 4, 20 and 24 h with HPLC. Table 1 shows the quantity of vitamin C produced from each substrate by *G. oxydans* DSM 4025 (FERM BP-3812).

TABLE 1

Vitamin C production from D-sorbitol, L-sorbose, L-sorbosone or L-gulose

| Substrate | Vitamin C produced [mg/L] | | |
|---|---|---|---|
| | 4 h | 20 h | 24 h |
| 8.0% D-Sorbitol | 0.0 | 62.3 | 90.3 |
| 8.0% L-Sorbose | 636.1 | 908.0 | 874.3 |
| 0.5% L-Sorbosone | 1,365.0 | 1,117.0 | 1,044.0 |
| 1.0% L-Gulose | 488.8 | 1,355.0 | 1,673.0 |
| None | 0.0 | 0.0 | 0.0 |

The invention claimed is:

1. A process for the production of vitamin C from D-sorbitol, L-sorbose, L-sorbosone or L-gulose comprising the steps of:
    (a) cultivating a microorganism in an aqueous nutrient-medium containing D-sorbitol, L-sorbose, L-sorbosone or L-gulose at a pH in the range of about 4.0 to about 9.0 and in a temperature range from about 13° C. to about 36° C. for about 1 to about 5 days, wherein the microorganism is selected from the group consisting of *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof, and
    (b) isolating and purifying the microbial produced vitamin C directly from the fermentation medium.

2. A process for the production of vitamin C from D-sorbitol, L-sorbose, L-sorbosone or L-gulose comprising cultivating a microorganism in an aqueous nutrient medium containing D-sorbitol, L-sorbose, L-sorbosone or L-gulose at a pH in the range of about 4.0 to about 9.0 and in a temperature range from about 13° C. to about 36° C. for about 1 to about 5 days and isolating microbially produced vitamin C directly from the fermentation broth and purifying the vitamin C by conventional methods, wherein the microorganism is selected from the group consisting of *Gluconobacter oxydans* DSM 4025 (FERM BP-3812), a microorganism belonging to the genus *Gluconobacter* and having identifying characteristics of *G. oxydans* DSM 4025 (FERM BP-3812) and mutants thereof.

3. A process according to claim 1 wherein the microorganism is *Gluconobacter oxydans* DSM 4025 (FERM BP-3812).

4. The process according to claim 1 wherein vitamin C is produced from L-gulose.

5. The process according to claim 1, wherein the process is carried out at a pH in the range of about 5.0 to about 8.0 and at a temperature range from about 18° to about 33° C. for 1 to 3 days.

6. A process according to claim 2 wherein the microorganism is *Gluconobacter oxydans* DSM 4025 (FERM BP-3812).

7. The process according to claim 2 wherein vitamin C is produced from L-gulose.

8. The process according to claim 2, wherein the process is carried out at a pH in the range of about 5.0 to about 8.0 and at a temperature range from about 18° to about 33° C. for 1 to 3 days.

* * * * *